United States Patent [19]

Lambert et al.

[11] Patent Number: 4,886,785
[45] Date of Patent: Dec. 12, 1989

[54] PYRIMIDINE DERIVATIVES, PHARMACEUTICAL COMPOSITIONS AND METHOD OF USING SAME

[75] Inventors: Robert W. Lambert, Welwyn; Joseph A. Martin, Harpenden; Gareth J. Thomas, Welwyn, all of England

[73] Assignee: Hoffmann-La Roche Inc., Nutley, N.J.

[21] Appl. No.: 79,730

[22] Filed: Jul. 30, 1987

[30] Foreign Application Priority Data

Aug. 12, 1986 [GB] United Kingdom ............... 8619630
May 7, 1987 [GB] United Kingdom ............... 8710775

[51] Int. Cl.$^4$ .................. A61K 31/70; C07H 17/00
[52] U.S. Cl. ............................... 514/50; 536/23
[58] Field of Search .................. 536/23; 514/49, 50

[56] References Cited

U.S. PATENT DOCUMENTS 4,000,260 12/1976 Prusoff et al. ............... 514/50
4,093,715  6/1978 Li et al. ...................... 536/23
4,093,716  6/1978 Li et al. ...................... 536/23

FOREIGN PATENT DOCUMENTS 2548190  1/1985 France .

OTHER PUBLICATIONS

Hampton et al., J. Med. Chem. 22, No. 12, pp. 1524–1528 (1979).
Journal of Medicinal Chemistry, vol. 24, No. 3, pp. 350–352 (1981).
Markham et al., Antiviral Research No. 2, pp. 319–330 (1982).

Primary Examiner—Johnnie R. Brown
Assistant Examiner—James Oliver Wilson
Attorney, Agent, or Firm—George M. Gould; Bernard S. Leon; Matthew Boxer

[57] ABSTRACT

Compounds of the formula

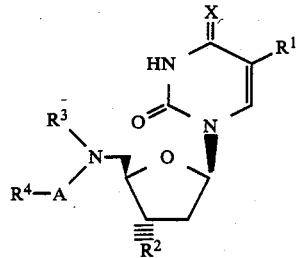

wherein A is $C_{1-8}$-alkylene, $R^1$ is halogen, $C_{1-4}$-alkyl or halo-($C_{1-4}$-alkyl), $R^2$ is hydrogen, hydroxy or acyloxy, $R^3$ is hydrogen or $C_{1-4}$-alkyl, $R^4$ is aryl or aryloxy and X is O or NH, and tautomers thereof are described. The compounds of formula I and their tautomers possess antiviral activity and can be used in the form of medicaments for the control and prevention of viral infections.

18 Claims, No Drawings

PYRIMIDINE DERIVATIVES, PHARMACEUTICAL COMPOSITIONS AND METHOD OF USING SAME

BRIEF SUMMARY OF THE INVENTION

The invention relates to pyrimidine derivatives, a process for their manufacture and medicaments containing said derivatives.

These pyrimidine derivatives are compounds of the formula

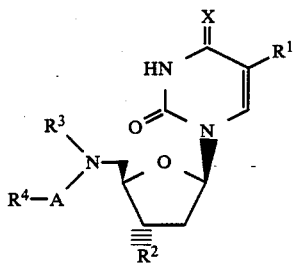

I wherein A is $C_{1-8}$-alkylene, $R^1$ is halogen, $C_{1-4}$-alkyl or halo-($C_{1-4}$-alkyl), $R^2$ is hydrogen, hydroxy or acyloxy, $R^3$ is hydrogen or $C_{1-4}$-alkyl, $R^4$ is aryl or aryloxy and X is O or NH, and tautomers thereof. The compounds of formula I and their tautomers are useful as agents in the control or prevention of viral infections.

DETAILED DESCRIPTION OF THE INVENTION

As used herein, "$C_{1-4}$-alkyl" means a straight- or branched-chain alkyl group, such as methyl, ethyl, propyl, isopropyl, butyl or t-butyl. "Halo-($C_{1-4}$-alkyl)" means an alkyl group as defined earlier carrying one or more halogen atoms; e.g. trifluoromethyl or 2-chloroethyl. "$C_{1-8}$-Alkylene" means a straight- or branched-chain alkylene group, such as —CH$_2$—, —CH$_2$CH$_2$—, —CH(CH$_3$)—, —CH$_2$CH$_2$CH$_2$—, —CH$_2$—CH(CH$_3$)— or —CH$_2$CH$_2$CH$_2$CH$_2$—. The acyloxy group can be derived from an aliphatic, cycloaliphatic, araliphatic or aromatic carboxylic acid, examples of such acids being formic acid, acetic acid, propionic acid, butyric acid, cyclopentylpropionic acid, phenylacetic acid and benzoic acid. Preferred acyloxy groups are $C_{1-4}$-alkanoyloxy groups. "Aryl" means unsubstituted phenyl or a phenyl group carrying one or more substituents selected from halogen, hydroxy, $C_{1-4}$-alkyl, $C_{1-4}$-alkoxy, trifluoromethyl, nitro and phenyl. Examples of such substituted-phenyl groups are 2-bromophenyl, 4-chlorophenyl, 2,3-dichlorophenyl, 2,6-dichlorophenyl, 2-methylphenyl and 2,6-dimethylphenyl. "Aryloxy" means an aryl group as defined earlier which is bonded via an oxygen atom. Examples of aryloxy groups are phenoxy, 4-chlorophenoxy, 2,4-dichlorophenoxy and 2,6-dichlorophenoxy. "Halogen" means fluorine, chlorine, bromine and iodine.

The invention relates to compounds of the formula

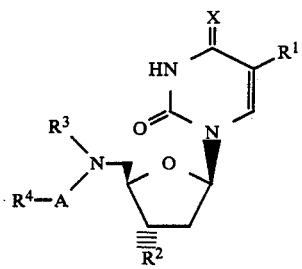

I wherein A is $C_{1-8}$-alkylene, $R^1$ is halogen, $C_{1-4}$-alkyl or halo-($C_{1-4}$-alkyl), $R^2$ is hydrogen, hydroxy or acyloxy, $R^3$ is hydrogen or $C_{1-4}$-alkyl, $R^4$ is aryl or aryloxy and X is O or NH, and tautomers thereof.

Depending on the significance of A in formula I, the compounds of formula I and their tautomers can be present as diastereoisomers. The present invention embraces within its scope not only the individual diastereoisomers, but also mixtures thereof.

In formula I above A preferably is $C_{1-4}$-alkylene, especially —CH$_2$—, —CH$_2$CH$_2$—, —CH(CH$_3$)— or —CH$_2$—CH(CH$_3$)—. $R^1$ preferably is $C_{1-4}$-alkyl, especially ethyl. $R^2$ preferably is hydroxy. $R^3$ preferably is hydrogen or methyl. $R^4$ preferably is dihalophenyl, especially 2,3- or 2,6-dichlorophenyl. X preferably is O. When A is —CH$_2$—CH(CH$_3$)— the compounds of formula I have the formula

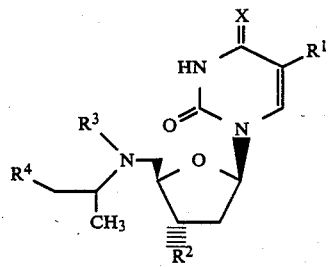

Especially preferred compounds of the invention are those in which A is —CH$_2$—, —CH$_2$CH$_2$—, —CH(CH$_3$)— or —CH$_2$—CH(CH$_3$)—, $R^1$ is ethyl, $R^2$ is hydroxy, $R^3$ is a hydrogen or methyl, $R^4$ is 2,3- or 2,6-dichlorophenyl and X is O.

Particularly preferred compounds are:

5'-(2,6-Dichlorobenzylamino)-2',5'-dideoxy-5-ethyluridine,

5'-[2-(2,6-dichlorophenyl)ethylamino]-2',5'-dideoxy-5-ethyluridine and

5'-(2,3-dichlorobenzylamino)-2',5'-dideoxy-5-ethyluridine.

Examples of other interesting compounds provided by the present invention are:

5'-(4-Chlorobenzylamino)-5'-deoxythymidine,

5'-(2-bromobenzylamino)-2',5'-dideoxy-5-ethyluridine,

5'-[2-(2-bromophenyl)ethylamino]-2',5'-dideoxy-5-ethyluridine,

2',5'-dideoxy-5-ethyl-5'-[2-(2,6-dimethylphenyl)ethylamino]uridine,

5'-(4-chlorobenzylamino)-2',5'-dideoxy-5-ethyluridine,

2',5'-dideoxy-5-ethyl-5'-[1(R)-phenylethylamino]uridine,

2',5'-dideoxy-5-ethyl-5'-[1(S)-phenylethylamino]uridine,

2',5'-dideoxy-5-ethyl-5'-(N-methylbenzylamino)uridine,

2',5'-dideoxy-5-ethyl-5'-(phenylethylamino)uridine,

2',5'-dideoxy-5-ethyl-5'-2-(2-methylphenyl)ethylamino]uridine,

2',5'-dideoxy-5-ethyl-5'-(N-methylphenylethylamino)uridine,

5'-[1(S)-benzylethylamino]-2',5'-dideoxy-5-ethyluridine,

5'-benzylamino-2',5'-dideoxy-5-ethyluridine,

2',5'-dideoxy-5-ethyl-5'-(2-methylbenzylamino)uridine and

5'-benzylamino-5'-deoxythymidine.

2',5'-Dideoxy-5-ethyl-5'-[2(RS)-(2,4-dichlorophenoxy)propylamino]uridine is an example of a further interesting compound provided by the present invention.

According to the process provided by the invention, the compounds of formula I above and their tautomers are manufactured by (a) reacting a compound of formula

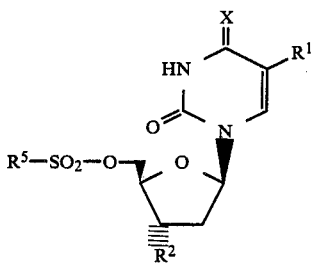

II wherein $R^1$, $R^2$ and X are as described above and $R^5$ is $C_{1-4}$-alkyl or aryl, or a tautomer thereof with a compound of the formula

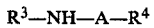

$R^3$—NH—A—$R^4$  III wherein A, $R^3$ and $R^4$ are as described above, at an elevated temperature, or (b) for the manufacture of a compound of formula I in which X is O or a tautomer thereof, introducing the group $R^4$—A— into a compound of formula

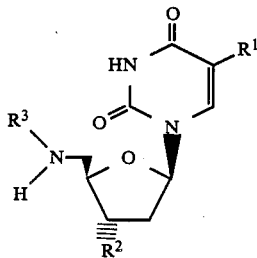

IV wherein $R^1$, $R^2$ and $R^3$ are as described above, or a tautomer thereof by reductive alkylation.

The reaction is accordance with embodiment (a) of the process is conveniently carried out in the presence of an inert organic solvent such as dimethylformamide (DMF), acetonitrile or dimethyl sulphoxide (DMSO). DMF is the preferred solvent and in this case the reaction mixture is suitably heated to a temperature of about 80° C. Alternatively, an excess of amine of formula III can be used and this can serve as the solvent. The group $R^5$ in formula II is preferably aryl, especially p-tolyl.

The reductive alkylation in accordance with embodiment (b) of the process can be carried out in a manner known per se. For example, a compound of formula IV or a tautomer thereof is reacted with an appropriate aldehyde or ketone and the resulting Schiff's base is then catalytically hydrogenated in situ to give the desired compound of formula I or tautomer thereof. The reductive alkylation is conveniently carried out in an inert organic solvent, expediently an alkanol, e.g. methanol or ethanol. The catalytic hydrogenation can be carried out under conventional conditions, e.g. using a noble-metal catalyst, such as a palladium or platinum catalyst, which may be supported on an inert carrier material. Palladium-on-carbon (Pd/C) is the preferred catalyst. Suitably, the catalytic hydrogenation is carried out at about room temperature and under atmospheric pressure. Alternatively, a compound of formula IV or a tautomer thereof can be reacted with an appropriate aldehyde or ketone in the presence of sodium cyanoborohydride in a suitable solvent, e.g. an aqueous alkanol such as aqueous methanol, expediently at room temperature.

The starting materials used in the above process, that is compounds of formulas II, III and IV, are known compounds or analogues of known compounds which can be prepared in a similar manner to the known compounds, e.g. as described hereinafter in the Examples.

The compounds of formula I and their tautomers possess antiviral activity and can be used in the control or prevention of viral infections, e.g. of herpes simplex viral infections.

The in vitro activity of the compounds of formula I and their tautomers in inhibiting herpes simplex virus type 2 (HSV-2) thymidine kinase can be demonstrated by means of the following test procedure:

In this test, the assay mixture contains 50 mM Tris-HCl, pH 8, 5 mM magnesium chloride, 5 mM ATP, 0.3 μM $^3$H-thymidine (50 Ci/mmol), suitably diluted thymidine kinase extract and various concentrations of compounds of formula I or tautomers in a total volume of 100 μl. Assays are incubated at 37° C. for 30 minutes and the reaction is terminated by immersion in a boiling water bath for 2 minutes. 85 μl aliquots from each assay are then dried on cellulose paper discs and the unphosphorylated $^3$H-thymidine is removed by washing in 4 mM ammonium formate. The radioactivity remaining bound to the discs is then measured by scintillation spectrophotometry. The degree of inhibition at each concentration of compound of formula I is expressed as a percentage of the control reaction (100%) after substracting a measured blank value which represents the amount of radioactivity bound to the disc from a reaction containing heat inactivated enzymes. The $IC_{50}$ value, namely the concentration of compound of formula I or tautomer thereof which inhibits enzyme activity by 50%, is then calculated. The results obtained with representative compounds of formula I are compiled in the following Table:

TABLE

| Compound of Example No. | $IC_{50}$ (μM) |
|---|---|
| 3b | 0.09 |
| 4b | 0.06 |
| 4c | 0.08 |

The compounds of formula I and their tautomers can be used as medicaments in the form of pharmaceutical preparations which contain them in association with a compatible pharmaceutical carrier material. This can be an organic or inorganic carrier suitable for enteral, e.g. oral, or parenteral administration. Examples of such carriers are water, gelatin, gum arabic, lactose, starch, magnesium stearate, talc, vegetable oils, polyalkylene glycols and petroleum jelly. The pharmaceutical preparations can be made up in a solid form, e.g. as tablets, dragees, suppositories or capsules, or in a liquid form, e.g. as solutions, suspensions or emulsions; they may be subjected to standard pharmaceutical operations, e.g. sterilization and/or may contain adjuvants, e.g. preserving, stabilizing, wetting or emulsifying agents, salts for varying the osmotic pressure or buffers. They may also contain other therapeutically valuable substances.

The compounds of formula I and their tautomers can be administered for the control or prevention of viral infection, such as herpes simplex viral infections, to warmblooded animals in need of such treatment.

The compounds of formula I and their tautomers can be administered to adult humans in a daily dosage of from about 1 to 1000 mg, preferably about 5 to 500 mg. The daily dosage may be administered as a single dose or in divided doses. The above dosage range is given by way of example only and can be varied upwards or downwards depending on factors such as the particular compound being administered, the route of administration, the severity of the indication being treated and the condition of the patient.

EXAMPLE 1

A solution of 396 mg of 5'-O-(p-toluenesulphonyl)-thymidine and 1.5 ml of 4-chlorobenzylamine in 2 ml of DMF was stirred at 80° C. for 2 hours. The solvent was removed by evaporation and the residue was triturated with diethyl ether. The resulting solid was recrystallized from ethanol to yield 56 mg of 5'-(4-chlorobenzylamino)-5'-deoxythymidine, mp 179°–180° C.

EXAMPLE 2

2.5 g of 2'-deoxy-5-ethyl-5'-O-(p-toluenesulphonyl)uridine were dissolved in 15 ml of DMF and added to 2-bromobenzylamine. The mixture was heated at 80° C. under nitrogen for 5 hours. The solvent was removed by evaporation and the residue was re-evaporated with toluene to given an oil. This was taken up in 20 ml of water/methanol (1:3) and stored in a refrigerator for 1.5 hours. A solid crystallized out and this was filtered off and washed with water/methanol (1:3) to give 0.99 g of 5'-(2-bromobenzylamino)-2',5'-dideoxy-5-ethyluridine, mp 144°–146° C.

The starting material, 2'-deoxy-5-ethyl-5'-O-(p-toluenesulphonyl)uridine, was prepared as follows:

26 g of 2'-deoxy-5-ethyluridine were dissolved in 400 ml of pyridine. The solution was cooled to 0° C. and stirred while 20 g of p-toluenesulphonyl chloride were added portionwise. Stirring was continued at 0° C. for 1 hour and the mixture was then stored at 4° C. overnight. The solvent was removed by evaporation and the residue was re-evaporated with toluene. The residue was shaken with 200 ml of methanol and left to stand in a refrigerator for 2.5 hours to give a solid which was filtered off, washed with methanol and dried to yield 18 g of product. Recrystallization from 450 ml of ethanol gave 13 g of 2'-deoxy-5-ethyl-5'-O-(p-toluenesulphonyl)uridine, mp 189°–190° C. (decomposition).

EXAMPLE 3

Analogously to Example 1, there were obtained:
(a) from 2'-deoxy-5-ethyl-5'-O-(p-toluenesulphonyl)uridine and 2-bromophenylethylamine:
5'-[2-(2-bromophenyl)ethylamino]-2',5'-dideoxy-5-ethyluridine, mp 109°–111° C.;
(b) from 2'-deoxy-5-ethyl-5'-O-(p-toluenesulphonyl)uridine and 2,6-dichlorophenylethylamine:
5'-[2-(2,6-dichlorophenyl)ethylamino]-2',5'-dideoxy-5-ethyluridine, mp 127°–128° C.; and
(c) from 2'-deoxy-5-ethyl-5'-O-(p-toluenesulphonyl)uridine and 2,6-dimethylphenylethylamine:
2',5'-dideoxy-5-ethyl-5'-[2-(2,6-dimethylphenyl)ethylamino]uridine, mp 73°–76° C.

EXAMPLE 4

Analogously to Example 2, there were obtained
(a) from 2'-deoxy-5-ethyl-5'-O-(p-toluenesulphonyl)uridine and p-chlorobenzylamine:
5'-(4-chlorobenzylamino)-2',5'-dideoxy-5-ethyluridine, mp 154°–156° C.,
(b) from 2'-deoxy-5-ethyl-5'-O-(p-toluenesulphonyl)uridine and 2,3-dichlorobenzylamine:
5'-(2,3-dichlorobenzylamino)-2',5'-dideoxy-5-ethyluridine, mp 158°–160° C.;
(c) from 2'-deoxy-5-ethyl-5'-O-(p-toluenesulphonyl)uridine and 2,6-dichlorobenzylamine:
5'-(2,6-dichlorobenzylamino)-2',5'-dideoxy-5-ethyluridine, mp 208°–210° C.;
(d) from 2'-deoxy-5-ethyl-5'-O-(p-toluenesulphonyl)uridine and 1(R)-phenylethylamine:
2',5'-dideoxy-5-ethyl-5'-[1(R)-phenylethylamino]uridine, mp 153° C. $[\alpha]_D^{20} = +27.1°$ (c=0.25% in DMSO);
(e) from 2'-deoxy-5-ethyl-5'-O-(p-toluenesulphonyl)uridine and 1(S)-phenylethylamine:
2',5'-dideoxy-5-ethyl-5'-[1(S)-phenylethylamino]uridine, mp 136° C., $[\alpha]_D^{20} = -19.5°$ (c=0.25% in DMSO);
(f) from 2'-deoxy-5-ethyl-5'-O-(p-toluenesulphonyl)uridine and N-benzylmethylamine:
2',5'-dideoxy-5-ethyl-5'-(N-methylbenzylamino)uridine, mp 135°–137° C.;
(g) from 2'-deoxy-5-ethyl-5'-O-(p-toluenesulphonyl)uridine and phenylethylamine:
2',5'-dideoxy-5-ethyl-5'-(phenylethylamino)uridine, mp 123°–125° C.;
(h) from 2'-deoxy-5-ethyl-5'-O-(p-toluenesulphonyl)uridine and 2-(2-methylphenyl)ethylamine:
2',5'-dideoxy-5-ethyl-5'-[2-(2-methylphenyl)ethylamino]uridine, mp 117° C.;
(i) from 2'-deoxy-5-ethyl-5'-O-(p-toluenesulphonyl)uridine and N-methyl-2-phenylethylamine:
2',5'-dideoxy-5-ethyl-5'-(N-methylphenylethylamino)uridine, mp 110° C.; and
(j) from 2'-deoxy-5-ethyl-5'-O-(p-toluenesulphonyl)uridine and d-amphetamine:
5'-[1(S)-benzylethylamino]-2',5'-dideoxy-5-ethyluridine, mp 150° C.; $[\alpha]_D^{20} = +23.4°$ (c=0.25% in DMSO).

EXAMPLE 5

A solution of 0.51 g of 5'-amino-2',5'-dideoxy-5-ethyluridine in 15 ml of ethanol was reacted under nitrogen with 0.21 ml of benzaldehyde. A slurry of 75 mg of 5% Pd/C catalyst in 5 ml of ethanol was then added and the mixture was hydrogenated at room temperature and under atmospheric pressure for 4.5 hours. The catalyst was filtered off. The filtrate was evaporated to give a foam which was triturated with diethyl ether, there being obtained 0.57 g of a solid. This solid was taken up in methylene chloride/methanol (9:1) and chromatographed on silica gel, eluting with methylene chloride/methanol. The fractions containing the product were combined and evaporated. The residue was triturated with diethyl ether and filtered off to give 0.45 g of 5'-benzylamino-2',5'-dideoxy-5-ethyluridine, mp 121°–124° C.

EXAMPLE 6

Analogously to Example 5, there were obtained (a) from 5'-amino-2',5'-dideoxy-5-ethyluridine and o-tolualdehyde;
  2',5'-dideoxy-5-ethyl-5'-(2-methylbenzylamino)uridine, mp 157°–158° C. and (b) from 5'-amino-5'-deoxythymidine and benzaldehyde: 5'-benzylamino-5'-deoxythymidine, mp 133°–135° C.

EXAMPLE 7

To a solution, cooled in ice, of 0.45 g of 5'-amino-2',5'-dideoxy-5-ethyluridine in 28 ml of methanol and 9 ml of water were added 0.17 g of sodium cyanoborohydride followed by 0.5 g of 2-(2,4-dichlorophenoxy)propionaldehyde. The mixture was allowed to warm to room temperature and was then stirred at room temperature for 3 days. The solution was concentrated in order to remove methanol, diluted with 20 ml of water and extracted three times with 15 ml of methylene chloride. The combined extracts were dried over sodium sulphate and evaporated. The residue was chromatographed on silica gel using methanol/methylene chloride (1:12) for the elution. There was obtained 0.26 g of 2',5'-dideoxy-5-ethyl-5'-[2(RS)-(2,4-dichlorophenoxy)-propylamino]uridine, mp 51°–61° C.

The 2-(2,4-dichlorophenoxy)propionaldehyde used as the starting material was prepared as follows:

43 ml of a 1M solution of borane in tetrahydrofuran (THF) were stirred under nitrogen and cooled in ice while a solution of 6.8 g of 2-(2,4-dichlorophenoxy)propionic acid in 40 ml of THF was added dropwise thereto. The mixture was heated to boiling under reflux for 1 hour and then cooled to room temperature. 22 ml of a saturated solution of hydrogen chloride in methanol were added dropwise and the solution was heated to boiling under reflux for 1 hour. The mixture was evaporated and the residue was treated with 22 ml of a saturated solution of hydrogen chloride in methanol. After heating under reflux for 1 hour the mixture was evaporated and the residue was partitioned between 100 ml of saturated sodium bicarbonate solution and 100 ml of methylene chloride. The layers were separated and the aqueous layer was extracted with 100 ml of methylene chloride. The combined organic extracts were dried over sodium sulphate and evaporated to gave 6.4 g of 2-(2,4-dichlorophenoxy)propanol as a yellow oil.

4.68 g of DMSO were added under nitrogen to a stirred solution of 3.81 g of oxalyl chloride in 75 ml of methylene chloride at −60° C. to −50° C. After 2 minutes a solution of 6.4 g of 2-(2,4-dichlorophenoxy)propanol in 40 ml of methylene chloride was added. The mixture was stirred at −60° C. for a further 15 minutes and was then treated with 13.7 g of triethylamine. After a further 5 minutes at −60° C. the mixture was allowed to warm to room temperature. 150 ml of water were added and the layers were separated. The aqueous layer was extracted with 150 ml of methylene chloride and the combined organic extracts were washed successively with sodium chloride solution, dilute hydrochloric acid, water, dilute sodium carbonate solution and water, dried over sodium sulphate and evaporated. The residue was purified by chromatography on silica gel using ethyl acetate/n-hexane (1:4) for the elution. There were obtained 1.4 g of 2-(2,4-dichlorophenoxy)propionaldehyde, mp 87°–88° C.

The following Example illustrates a pharmaceutical preparation containing a compound of formula I:

Tablets containing the following ingredients may be prepared in a conventional manner:

| Ingredient | Per tablet |
| --- | --- |
| Compound of formula I | 100 mg |
| Lactose | 70 mg |
| Maize starch | 70 mg |
| Polyvinylpyrrolidone | 5 mg |
| Magnesium stearate | 5 mg |
| Tablet weight | 250 mg |

We claim:

1. A compound of the formula

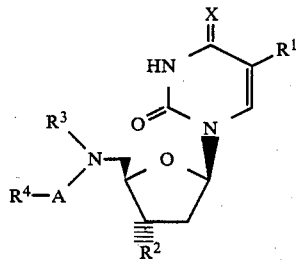

wherein A is $C_{1-8}$-alkylene, $R^1$ is halogen, $C_{1-4}$-alkyl or halo-($C_{1-4}$-alkyl), $R^2$ is hydrogen, hydroxy $C_{1-4}$-alkanoyloxy, cyclopentylproprionyloxy, phenylacetoxy, or benzoyloxy, $R^3$ is hydrogen or $C_{1-4}$-alkyl, $R^4$ is unsubstituted phenyl or phenyl carrying one or more substituents selected from the group consisting of halogen, hydroxy, $C_{1-4}$-alkyl, $C_{1-4}$-alkoxy, trifluoromethyl, nitro and phenyl or an unsubstituted phenyloxy or phenyloxy carrying one or more substituents selected from the group consisting of halogen, hydroxy, $C_{1-4}$-alkyl, $C_{1-4}$-alkoxy, trifluoromethyl, nitro and phenyl and X is O or NH, or a tautomer thereof.

2. A compound according to claim 1, wherein $R^5$ is unsubstituted phenyl or phenyl carrying one or more substituents selected from the group consisting of halogen, hydroxy, $C_{1-4}$-alkyl, $C_{1-4}$-alkoxy, trifluoromethyl, nitro and phenyl.

3. A compound according to claim 1, wherein A is $C_{1-4}$-alkylene.

4. A compound according to claim 1, wherein $R^1$ is $C_{1-4}$-alkyl.

5. A compound according to claim 1, wherein $R^2$ is hydroxy.

6. A compound according to claim 1, wherein $R^3$ is hydrogen or methyl.

7. A compound according to claim 1, wherein $R^4$ is dihalophenyl.

8. A compound according to claim 1, wherein X is O.

9. A compound according to claim 1, wherein A is —CH$_2$—, —CH$_2$CH$_2$—, —CH(CH$_3$)— or —CH$_2$—CH(CH$_3$)—, R$^1$ is ethyl, R$^2$ is hydroxy, R$^3$ is hydrogen or methyl, R$^4$ is 2,3- or 2,6-dichlorophenyl and X is O.

10. A compound according to claim 1, selected from the group consisting of
5'-(2,6-Dichlorobenzylamino)-2',5'-dideoxy-5-ethyluridine,
5'-[2-(2,6-dichlorophenyl)ethylamino]-2',5'-dideoxy-5-ethyluridine and
5'-(2,3-dichlorobenzylamino)-2',5'-dideoxy-5-ethyluridine.

11. A compound according to claim 2, selected from the group consisting of
5'-(4-Chlorobenzylamino)-5'-deoxythymidine,
5'-(2-bromobenzylamino)-2',5'-dideoxy-5-ethyluridine,
5'-[2-(2-bromophenyl)ethylamino]-2',5'-dideoxy-5-ethyluridine,
2',5'-dideoxy-5-ethyl-5'-[2-(2,6-dimethylphenyl)ethylamino]uridine,
5'-(4-chlorobenzylamino)-2',5'-dideoxy-5-ethyluridine,
2',5'-dideoxy-5-ethyl-5'-[1(R)-phenylethylamino]uridine,
2',5'-dideoxy-5-ethyl-5'-[1(S)-phenylethylamino]uridine,
2',5'-dideoxy-5-ethyl-5'-(N-methylbenzylamino)uridine,
2',5'-dideoxy-5-ethyl-5'-(phenylethylamino)uridine,
2',5'-dideoxy-5-ethyl-5'-[2-(2-methylphenyl)ethylamino]uridine,
2',5'-dideoxy-5-ethyl-5'-(N-methylphenylethylamino)uridine,
5'-[1(S)-benzylethylamino]-2',5'-dideoxy-5-ethyluridine,
5'-benzylamino-2',5'-dideoxy-5-ethyluridine,
2',5'-dideoxy-5-ethyl-5'-(2-methylbenzylamino)uridine and
5'-benzylamino-5'-deoxythymidine.

12. A compound in according with claim 1, 2',5'-dideoxy-5-ethyl-5'-[2(RS)-(2,4-dichloro-phenoxy)-propylamino]uridine.

13. A composition comprising an amount effective for inhibiting herpes simplex virus type 2 (HSV-2) thymidine kinase in vitro of a compound of the formula

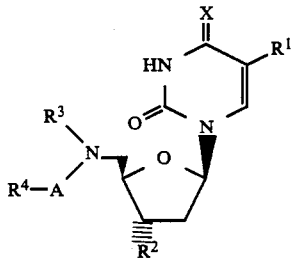

wherein A is C$_{1-8}$-alkylene, R$^1$ is halogen, C$_{1-4}$-alkyl or halo-(C$_{1-4}$-alkyl), R$^2$ is hydrogen, hydroxy C$_{1-4}$-alkanoyloxy, cyclopentylpropionyloxy, phenylacetoxy, or benzoyloxy, R$^3$ is hydrogen or C$_{1-4}$-alkyl, R$^4$ is unsubstituted phenyl or phenyl carrying one or more substituents selected from the group consisting of halogen, hydroxy, C$_{1-4}$-alkyl, C$_{1-4}$-alkoxy, trifluoromethyl, nitro and phenyl or an unsubstituted phenyloxy or phenyloxy carrying one or more substituents selected from the group consisting of halogen, hydroxy, C$_{1-4}$-alkyl, C$_{1-4}$-alkoxy, trifluoromethyl, nitro and phenyl and X is O or NH, or a tautomer thereof and a compatible pharmaceutical carrier material.

14. A composition in accordance with claim 13, wherein R$^4$ is unsubstituted phenyl or phenyl carrying one or more substituents selected from the group consisting of halogen, hydroxy C$_{1-4}$-alkyl, C$_{1-4}$-alkoxy, trifluoromethyl, nitro and phenyl.

15. Composition in accordance with claim 13, wherein the compound of formula I is 2',5'-dideoxy-5-ethyl-5'-[2(RS)-(2,4-dichlorophenoxy)propylamino]uridine.

16. A method for inhibiting herpes simplex virus type 2 (HSC-2) thymidine kinase in vitro which comprises administering an amount effective for inhibiting herpes simplex virus type 2 (HSV-2) thymidine kinase of a compound of the formula

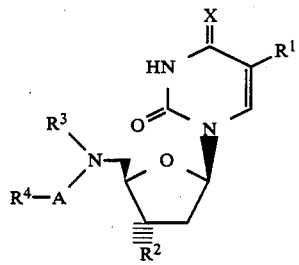

wherein A is C$_{1-8}$-akylene, R$^1$ is halogen, C$_{1-4}$-alkyl or halo-(C$_{1-4}$-alkyl), R$^2$ is hydrogen, hydroxy C$_{1-4}$-alkanoyloxy, cyclopentylpropionyloxy, phenylacetoxy, benzoyloxy, R$^3$ is hydrogen or C$_{1-4}$-alkyl, R$^4$ is unsubstituted phenyl or phenyl carrying one or more substituents selected from the group consisting of halogen, hydroxy, C$_{1-4}$-alkyl, C$_{1-4}$-alkoxy, trifluoromethyl, nitro and phenyl or an unsubstituted phenyloxy or phenyloxy carrying one or more substituents selected from the group consisting of halogen, hydroxy, C$_{1-4}$-alkyl, C$_{1-4}$-alkoxy, trifluoromethyl, nitro and phenyl, and X is O or NH, or a tautomer thereof.

17. A method in accordance with claim 16, wherein R$^4$ is unsubstituted phenyl or phenyl carrying one or more substituents selected from the group consisting of halogen, hydroxy C$_{1-4}$-alkyl, C$_{1-4}$-alkoxy, trifluoromethyl, nitro and phenyl.

18. A method in accordance with claim 16, wherein the compound of formula I is 2',5'-dideoxy-5-ethyl-5'-[2(RS)-(2,4-dichlorophenoxy)propylamino]uridine.

* * * * *